United States Patent [19]

Bellotti et al.

[11] Patent Number: 4,821,996
[45] Date of Patent: Apr. 18, 1989

[54] FLUID FLOW CONTROL VALVE AND TRANSFER SET

[75] Inventors: Marc Bellotti; William J. Schnell, both of Libertyville; John F. Love, Prairie View, all of Ill.; Randy K. Murphey, Kenosha, Wis.; Larry C. Taylor, McHenry, Ill.; Franco Peluso, Leuven, Belgium

[73] Assignee: Baxter Travenol Laboratories, Inc., Deerfield, Ill.

[21] Appl. No.: 8,012

[22] Filed: Jan. 28, 1987

[51] Int. Cl.⁴ .............................................. F16K 7/06
[52] U.S. Cl. .................................... 251/9; 251/4; 251/230; 604/34
[58] Field of Search .................. 251/4, 7, 9, 230; 137/862, 863, 867; 604/32-34

[56] References Cited

U.S. PATENT DOCUMENTS

| | | |
|---|---|---|
| D. 250,085 | 10/1978 | Tuttle . |
| 2,838,270 | 6/1958 | Danielson ..................... 251/230 X |
| 3,016,915 | 9/1959 | Moeller . |
| 3,411,534 | 12/1968 | Rose . |
| 3,444,896 | 5/1969 | Van Ner Veer ............... 251/230 X |
| 3,459,182 | 8/1966 | Naftulin . |
| 3,515,170 | 12/1967 | Mullaly . |
| 3,575,161 | 4/1971 | London . |
| 3,805,842 | 4/1974 | Thompson et al. . |
| 3,918,490 | 11/1975 | Goda . |
| 3,920,215 | 11/1975 | Knauf ..................................... 251/7 |
| 3,960,224 | 6/1976 | Silvers . |
| 3,985,134 | 10/1976 | Lissot et al. . |
| 4,061,142 | 12/1977 | Tuttle . |
| 4,360,007 | 11/1982 | Levy et al. ...................... 251/7 X |
| 4,425,113 | 1/1984 | Bilstad . |
| 4,425,116 | 1/1984 | Bilstad et al. . |
| 4,428,745 | 1/1984 | Williams . |
| 4,457,339 | 7/1984 | Juan et al. ...................... 251/7 X |

FOREIGN PATENT DOCUMENTS 2700491  3/1978  Fed. Rep. of Germany .

Primary Examiner—A. Michael Chambers
Assistant Examiner—John C. Fox
Attorney, Agent, or Firm—Paul C. Flattery; Daniel D. Ryan; Charles R. Mattenson

[57] ABSTRACT

A multi-position rotary valve system is useable with a disposable fluid transfer set for carrying out a sequence of steps to implement a drain and fill procedure in connection with peritoneal dialysis. A method of carrying out peritoneal dialysis includes utilizing a rotary, multi-position, valve system in conjunction with a fluid flow transfer set having a plurality of flexible fluid flow conduits. The valve system provides for systematically opening and closing the respective fluid flow conduits in a predetermined sequence for the purpose of carrying out a drain and fill procedure of the type associated with peritoneal dialysis.

47 Claims, 7 Drawing Sheets

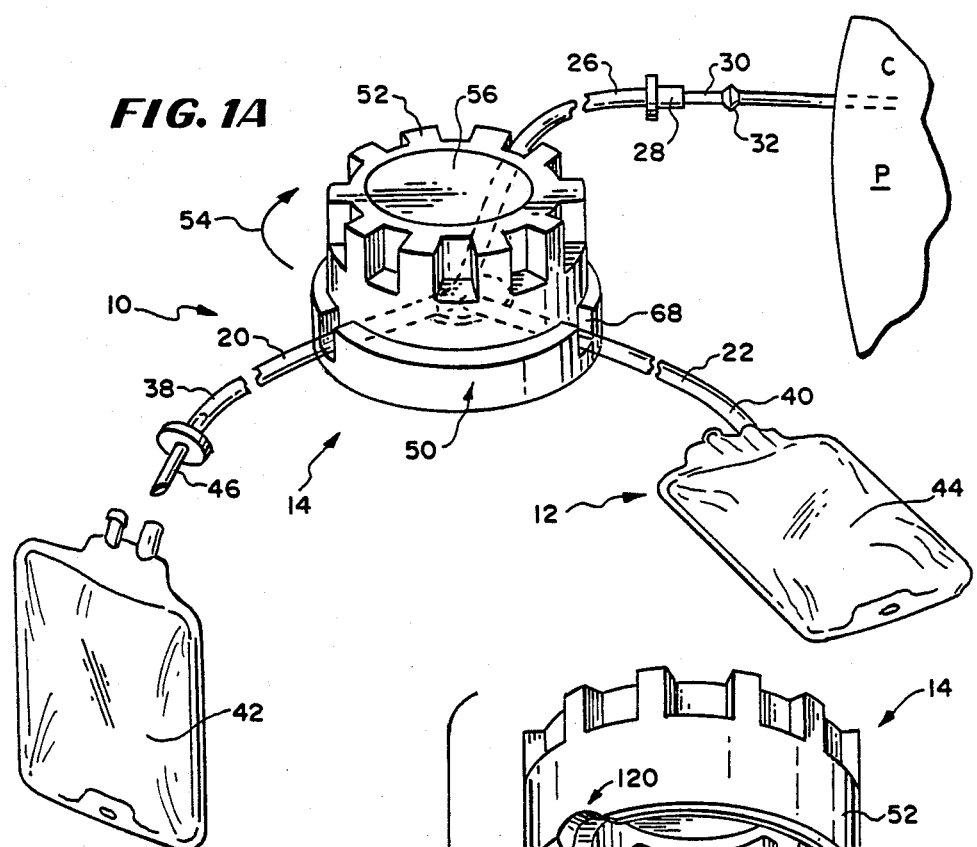
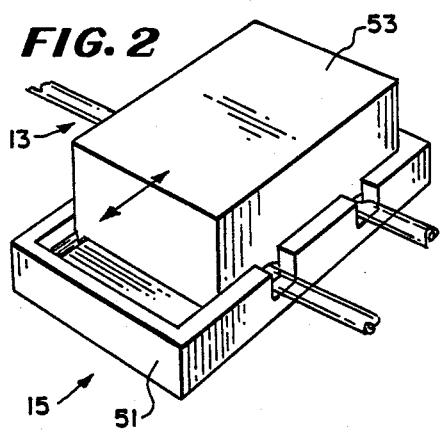
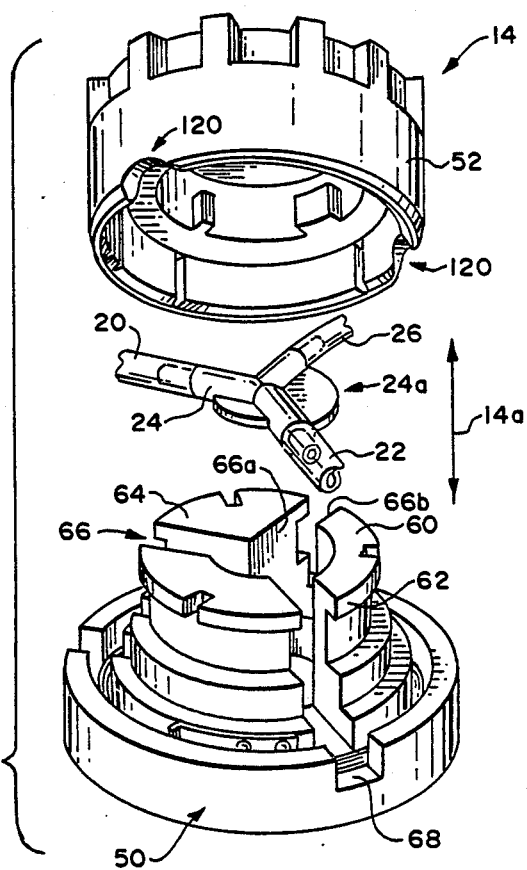
FIG. 1A
FIG. 2
FIG. 1B

FLUID FLOW CONTROL VALVE AND TRANSFER SET

FIELD OF THE INVENTION

The invention pertains to methods and devices useable in connection with carrying out peritoneal dialysis. More particularly, the invention pertains to a valve system, fluid transfer set and method which facilitate executing the steps of a drain and fill cycle associated with continuous ambulatory peritoneal dialysis.

BACKGROUND OF THE INVENTION

Two general types of dialysis therapy are now in wide spread use. One type, hemodialysis provides for removing waste products by passing the blood of a patient through an appropriately constructed dialyzer unit. A second type of dialysis therapy, peritoneal dialysis, utilizes the membrane in a patient's peritoneal cavity for the purpose of separating waste products from the patient's fluid systems.

In one form of peritoneal dialysis, referred to as continuous ambulatory peritoneal dialysis (CAPD), dialysis fluid is introduced into the patient's peritoneal cavity by means of an in-dwelling peritoneal catheter. The dialysis solution is permitted to remain in the peritoneal cavity of the patient for a time interval on the order four to six hours. At the end of this time interval, spent fluid is drained from the patient's cavity, under the influence of gravity, and fresh dialysis fluid is infused into the cavity to continue the process.

The drain and fill cycle noted above is carried out best where the patient systematically executes a predetermined sequence of steps to first drain spent fluid and then to refill the peritoneal cavity with fresh fluid. Carrying out the predetermined sequence of steps requires opening and closing, in a predetermined sequence, a plurality of flexible tubing members in a fluid flow transfer set connected between the external end of the patient's catheter and solution containers of peritoneal dialysis fluid.

One valve system useable in carrying out this procedure is illustrated in U.S. Pat. No. 4,239,041 to Popovich et al. entitled "Method For Continuous Ambulatory Peritoneal Diaylsis." The valve system of the Popovich et al. patent is integrally formed with the transfer set disclosed therein. The transfer set including the valve system is of a type that would be worn by the patient for an extended period of time.

Since the Popovich et al. valve system is intended to be carried about the patient's person, it of necessity must be formed to be relatively small and light weight. Hence, there are substantial limits as to the mechanical advantage that can be obtained with such a structure. The Popovich et al. valve system must also be formed out of material that can be sterilized during the manufacturing process of the set. In addition, the Popovich et al. valve system must be formed of material which is suitable for long term patient contact and which can be periodically flushed with disinfectant solution.

U.S. Pats. Nos. 4,425,113 and 4,428,745 issued respectively to Bilstad and Williams disclose several mechanical fluid flow control valves for use with fluid transfer sets. These valves are formed with a base into which can be placed a portion of the transfer set. A hinged top, attached to the base can then be closed over the base. A moveable flow control member attached to the top can be used to close various of the fluid flow conduits that extend into the base. The disclosed valves are illustrated in connection with transfer sets usable for plasma pheresis.

There thus contains to be a need for a valve system and related set which provides reasonable mechanical advantage to the patient while opening and closing the fluid flow conduits of the set. In addition, there continues to be a need for a valve system which is reusable and which can readily be utilized with single use transfer sets without compromising the sterile or aseptic condition of the internal lumens of the fluid flow conduits of the set.

SUMMARY OF THE INVENTION

A valve system is provided which can be used in combination with a plurality of interconnected fluid flow conduits. The valve system operates external to the fluid flow conduits in a noninvasive manner, to selectively control fluid flow through the conduits without contacting the fluid itself. The valve system includes a base which can receive in spaced apart relationship the plurality of interconnected fluid flow conduits. A selecting member can be removably affixed to the base for selectively blocking fluid flow through the members of the plurality of conduits.

In one particular embodiment, the base member can be generally circular in shape. The selecting means in this instance can be a generally cylindrical member removably and rotatably mountable on the base member.

In another embodiment, the fluid flow conduits can be interconnected so as to form a fluid transfer set. The transfer set can be used in carrying out various medical treatment modalities. One particular modality that the valve system and the transfer set are especially suited to is continuous ambulatory peritoneal dialysis (CAPD).

The selecting member can be removed from the base member and the transfer set can be positioned in the base member. The transfer set may have a keyed central region which engages a mating region in the base member in order that the set can be installed with a desired orientation. In one embodiment, the key is affixed to a centrally-located coupling member of the set. A mating corresponding region can be centrally located on the base member.

Apertures are provided so that the fluid flow conduits of the set can be properly spaced around the base member. When the selecting member is removably attached to the base member, a lower, discontinuous annular surface thereof is brought into contact with outside walls of various members of the plurality of fluid flow conduits. Force applied by the lower annular surface against the flexible conduits clamps them shut and blocks any flow of fluid therethrough. The selecting member also includes one or more selectively shaped apertures or recesses which intersect the annular surface. When an aperture is positioned adjacent a selected fluid flow conduit, fluid can flow through that conduit.

An indexing member may also be provided. The indexing member is affixed to the base member and slidably engages the rotatable selecting member. The indexing member defines a plurality of angularly spaced apart index positions through which the selecting member can be rotated.

As the selecting member is rotated through this sequence of positions, various members of the plurality of fluid flow conduits are unclamped by the respective recess or aperture so fluid can flow therethrough. The indexing member also includes provision for permitting rotation only in one direction. Rotation in the opposite direction is blocked by the interaction between the indexing member and the selecting member.

In an alternate form of the valve system, the base member can be elongated and the selecting member can be linearly displaceable along the base member. In this embodiment, the selecting member can be moved from end to end of the base member thereby opening and closing a predetermined sequence of fluid flow conduits.

It is a particularly important aspect of the present invention that, because of the mechanical advantage present, the valve system is readily operable with limited amounts of manually applied force. Hence, even a person of limited strength can rotate the selecting member or move it linearly through the predetermined sequence of positions.

In yet another embodiment of the invention, the circular base member and the selecting member can each be provided with a set of threads. The selecting member can be aligned with the base member and then rotated so as to threadably engage the base member. This allows easier assemblage of the selecting member and the base. Additional mechanical advantage can be provided between the selecting member and the base.

Further, a method is provided of carrying out a drain and fill cycle of a peritoneal dialysis treatment. The method includes providing a selected fluid flow transfer set. The transfer set has first and second sections of branch tubing. Distal ends of the tubing sections are connectable to dialysis solution containers. Proximal ends of the tubing sections are coupled to branches of a fluid flow "Y" junction member. The "Y" junction member has a central portion coupled to a proximal end of a central section of tubing. The central section of tubing has a distal end that can be placed in fluid flow communication with the catheter of a patient.

The "Y" junction may be formed with a selectively shaped key. This key can be positioned in the base portion of the valve with one or more desired orientations.

The method includes: placing the set in the valve with the key engaging the base member and the three tubing sections extending through respective apertures in the base member;

placing the selecting member on the base member and rotating it to a first index position thereby blocking flow through all conduits;

placing a first branch tubing member into fluid communication with a fresh bag of dialysis solution;

attaching the central tubing member to the catheter of the patient;

rotating the selecting member to a next index position, coupling the two branch tubing members together, and thereby permitting fluid to flow from the container of dialysis solution to the distal end of the other branch tubing member flushing those branch tubing members;

rotating the selecting member to a next index position, coupling the central tubing member to the second branch tubing member, and thereby permitting spent dialysis fluid to flow from the patient's catheter, through the central tubing member, the junction member, the second branch tubing member and out the distal end of the second tubing member;

rotating the selection member to a next index position, coupling the central tubing member to the first branch tubing member, and thereby permitting fresh dialysis solution to flow from the container into the catheter of the patient; and rotating the selecting member to a next index position closing all tubing members of the set.

The transfer set can then be disconnected from the patient's catheter. The selecting member can be rotated to a final position at which it can be removed from the base member. The set can then be removed from the base member.

In one form of the invention, the transfer set can be a single use set. An empty dialysis solution container can be affixed to the tubing while the set is being manufactured. The empty container can be used to accumulate the spent dialysis solution. The set can then be disposed of. Alternately, a multi-use, reusable set can be used. The reusable set can be stored apart from the patient during the dwell cycle, between drain and fill cycles.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 1A is a perspective view of a peritoneal dialysis system with a valve system in accordance with the present invention;

FIG. 1B is an enlarged perspective view of the valve system with a fragmentary view of an associated fluid transfer set in accordance with the present invention;

FIG. 2 is a perspective view of an alternate valve system;

DETAILED DESCRIPTION OF THE PREFERRED EMBODIMENT

Figure 3:
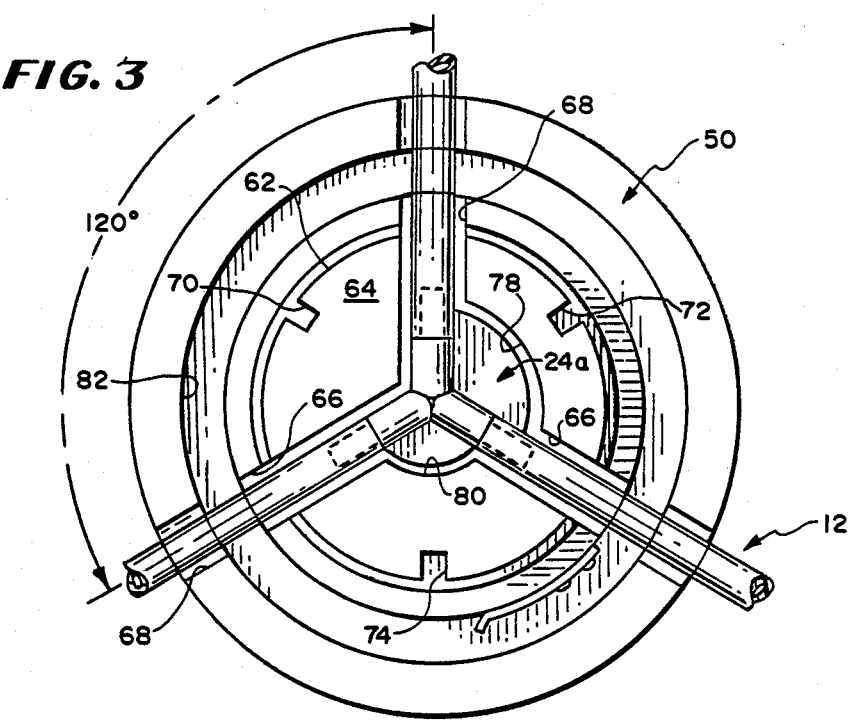
FIG. 3 is a top plan view of a base member of a valve system in accordance with the present invention.

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

FIG. 1A illustrates a system 10 in accordance with the present invention. The system 10 is in fluid flow communication with a peritoneal catheter C of a patient P. The system 10 facilitates and assists the patient P in carrying out the drain and fill cycles required several times a day in connection with continuous ambulatory peritoneal dialysis (CAPD). The system 10 provides a way to proceed very systematically through the necessary steps of each drain and fill cycle to minimize the possibility of the omission of steps and to minimize the possibility of the interchange of steps.

The system 10 includes two major components. The first component is a fluid transfer set 12. The second component is a reusable rotary valve system 14 which receives a section of the transfer set 12 for the purpose of regulating fluid flow to and from the patient P by means of selected flexible conduit members of the set 12.

The set 12 may be variously constructed. In the illustrated embodiment, the set 12 includes first and second flexible, preferably elastic or plastic, fluid flow conduits 20 and 22. Each of the conduits 20 and 22 is in fluid flow communication at a proximal end with a fluid flow Y junction 24. The junction 24 is also in fluid flow communication with a central tubing member 26.

The tubing member 26 is couplable via a standard tubing connector member 28 to a relatively short exchange set 30. The exchange set 30 can be removably coupled to an external end of the catheter C by a standard titanium catheter connector 32 of a commercially available type. Alternately, the connector 28 on the tubing member 26 could be directly connected to the catheter connector 32.

Distal ends 38 and 40 of tubing members 20 and 22 can be coupled to first and second dialysis solution containers 42 and 44. The containers 42 and 44 can be removably coupled to the distal ends 38 and 40 by means of standard spike connectors, such as the spike connector 46 illustrated in FIG. 1. Alternately, if the container 42 is utilized to provide a fresh quantity of dialysis solution and container 44 is utilized to collect a quantity of spent dialysis solution from the patient P, the set 12 can be fabricated as a single use set with an empty dialysis solution container, such as the container 44, fixedly attached to the distal end 40.

The valve system 14 has a circular base assembly 50 and a flow controlling rotary, removably engageable, selection ring 52. The selection ring 52 is slidably received on the base member 50 at only one rotational insertion-removal position, with respect to the base 50.

Arrow 14a indicates linear movement of the ring 52 onto and away from the base 50 at the insertion-removal position. The selection ring 52 is rotatable in only one direction 54 through a sequence of predetermined positions for the purpose of closing and opening the fluid flow conduits 20, 22 and 26 of the set 12 in a predetermined sequence to carry out a drain and fill cycle as required by the patient P. A circular cap 56 can be used to close the top of the selection ring 52.

Use of the valve system 14 is particularly advantageous in that a substantial mechanical advantage is provided by the selection ring 52 such that even a person of limited, physical strength can readily open and close the required conduits. Further, use of the valve system 14 insures that the conduits 20, 22 and 26 will be opened and closed only in a predetermined sequence of the type necessary to carry out the desired drain and fill portion of the dialysis procedure.

The valve system 14 is also advantageous in that it is reusable by the patient P. Further, since the valve system 14 exerts pressure external to the conduits 20, 22 and 26 of the set 12, there is no possibility that it will impair the sterility or the aseptic condition of the set 12 during the drain and fill cycle.

As can be seen from FIG. 1B, the base member 50 includes an upper, generally cylindrical portion 60 with a discontinuous, radially directed flange 62 formed on an upper surface 64. The flange 62 provides a locking member, fixed with respect to the base 50, which slidably engages a mating member formed within the selection ring 52 for the purpose of rotatably locking the selection ring 52 to the base 50 except at the single insertion-removal location.

When being used to conduct a drain and fill procedure, the system 10 can be positioned on a flat surface, such as a table. The base member 50, which preferably light weight, can include a nonskid bottom, such as by using friction pads or suction cups, so that the selection ring 52 may be rotated by the patient P without the necessity of holding or restraining the base portion 50.

The upper cylindrical section 60 also includes a plurality of spaced, axially directed slots 66. Each of the slots 66 is formed with first and second spaced apart, axially directed surfaces 66a and 66b. In the illustrated embodiment, the slots 66 are spaced at 120 degree intervals around the cylindrical section 60. However, the degree of arcuate spacing can vary and is not a limitation on the present invention. The tubing members 20, 22 and 26 are intended to extend through the slots 66 as illustrated in FIG. 1A. Each of the slots 66 includes a radially extending lower portion 68 on which the respective tubing members 20, 22 and 26 are positioned. The radially extending portions 68 provide means which cooperate with the rotatable selection ring 52 to clamp or close off the respective tubing members.

In summary, the patient P places the valve system 14 on a flat surface, and installs the set 12 therein. In the illustrated embodiment, the junction member 24 carries a selectively shaped region or key 24a, so that the set 12 can be properly inserted into the valve system 14 with only one orientation. This assists the patient in properly aligning the set 12 relative to the valve system 14. The key 24a can be variously configured, according to the configuration and manipulation required of the set 12. Alternately, the set 12 could be without a key 24a, placing the orientation of the set 12 within the valve system 14 entirely in the patient's discretion. The patient then couples the set 12 to the exchange set 30, and couples a fresh bag 42 of dialysis solution to the set 12.

By rotating the selection ring 52, the patient P can proceed through the necessary drain and fill cycle. Upon completion of the fill phase of the cycle, the selection ring can be rotated into a shut-off position, the set 12 is uncoupled from the exchange set 30. The selection ring 52 is then rotated into its insertion-removal position and removed from the base 50. The set 12 can then be removed from the base 50 and stored for use in a subsequent exchange session. It could, for example, be stored in the closed O-shaped configuration disclosed in co-pending U.S. patent application Ser. No. 552,936 entitled "Detachable Peritoneal Dialysis Set." Alternately, the set 12 can be disposed of, and a new set 12 used in the next subsequent exchange session.

FIG. 2 illustrates an alternate valve system 15. The valve system 15 includes a base 51 and a linearly displaceable selection member 53. A fluid flow transfer set 13 can be positioned on the base 51. The selection member 53 can be moved linearly so as to open and close the fluid flow members of the set in a predetermined sequence.

FIG. 3 is a top view of the base 50 with the set 12 positioned therein. The axially oriented slots 66 are spaced at 120 degree intervals around the base 50. The discontinuous, radially extending flanges 62 are shown formed adjacent the upper surface 64 of the cylindrical housing member 60.

Positioned between the tubing receiving slots 66 are three additional spaced-apart orientation defining, radially oriented slots 70, 72 and 74. The slots 70 through 74 define the insertion-release position of the selection ring 52 with respect to the base 50. The slots 70 and 72 are offset with respect to the slot 74 such that the rotary selection member 52 can only be rotatably engaged with the flanges 62 when correctly aligned with respect to the orientation slots 70, 72 and 74.

Centrally located on the base 50 is a two-part key 78 and 80. The key formed of the parts 78 and 80 cooperates with the correspondingly-shaped key 24a of the Y junction member 24 to insure that the set 12 can only be inserted into the base 50 with a single orientation. The key member 24a has a web or key section with a 120° arc and a first radius and a web or key section with a 120° arc and a second, smaller radius. The asymmetrical structure of the sections 78, 80 of the base member 50 cooperates with the asymmetrical structure of key member 24a such that the set 12 can be properly inserted into the base 50 with only one orientation.

Alternately, the key 24a can be formed with various other configurations using, for example, differing arcs with each arc having the same or different radius.

An annular slot 82 is provided in the base section 50. The annular slot 82 intersects the radially-directed lower portions 68 of the tubing receiving slots 66. As is discussed subsequently, a flexible member is positioned in the annular slot 82 against which the corresponding tubing member can be clamped closed.

Figure 4:
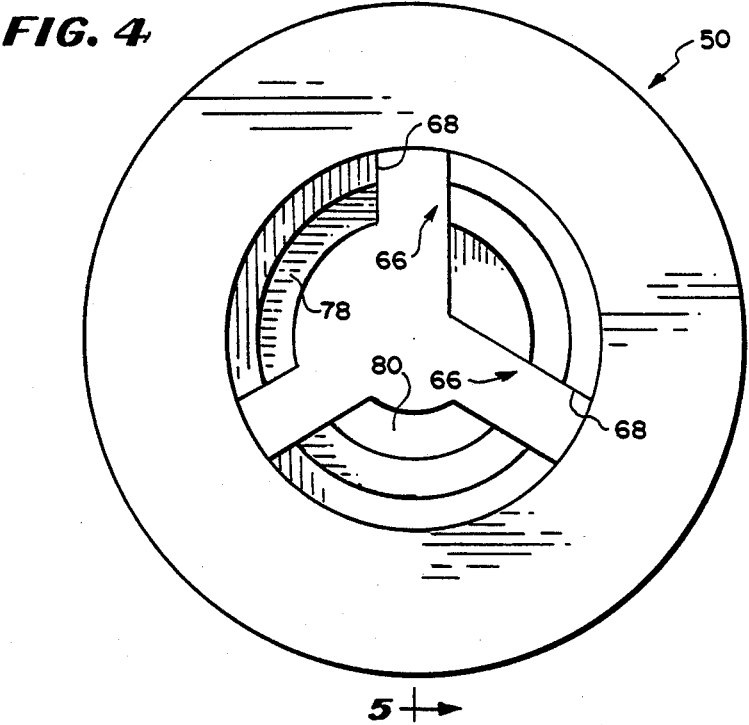
FIG. 4 is a bottom plan view of the base member of the valve system in accordance with the present invention.

FIG. 4 is a bottom view of the base 50. The overall relationship between the spaced apart key members 78 and 80 and the axially extending tubing receiving slots 66 can be seen in FIG. 3.

Figure 5:
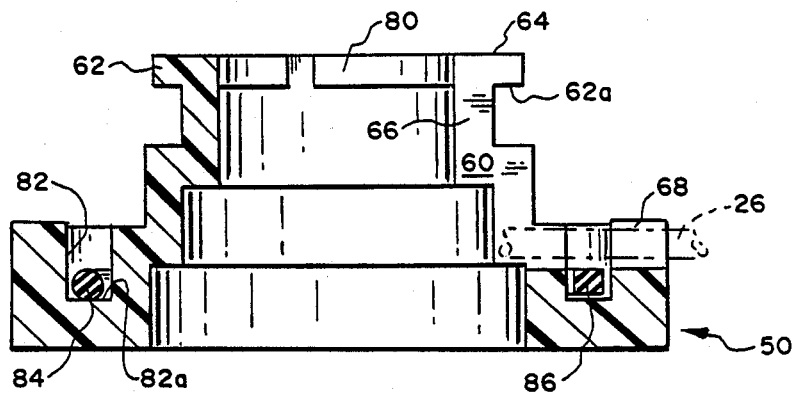
FIG. 5 is a view in section of the base member taken along plane 5-5 of FIG. 4.

FIG. 5, a view in section of the base 50 taken along plane 5—5 of FIG. 4, further illustrates the structure of the base member 50. The discontinuous radially extending flange 62 can be seen in FIG. 5. A lower bearing surface 62a of the flange 62 provides a surface against which the selection ring 52 can slidably rotate.

FIG. 5 also illustrates the annular slot 82 utilized in connection with clamping shut the various tubing members, such as the fragmentary portion of the tubing member 26. Positioned in the annular slot 82 is either an O-ring 84 or a flat, circular gasket 86. The O-ring 84 or the gasket 86 could be formed of a variety of resilient materials.

The members 84 and 86 provide a deformable surface against which portions of the respective tubing members 20, 22 and 26 can be forced and clamped for the purpose of closing off fluid flow therethrough. As is discussed subsequently, the annular slot 82 and the resilient member 84 or 86 cooperate with an axially extending force applying member in the selection ring 52 for the purpose of clamping a part of respective tubing member therebetween.

Figure 6:
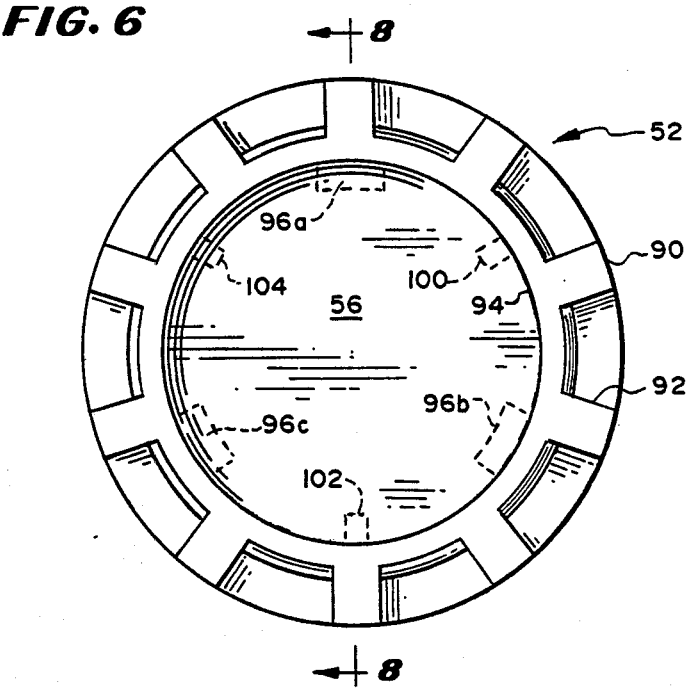
FIG. 6 is a top plan view of a rotary selection member removably mountable on the base member of the valve system and illustrated with a closing cap.

FIG. 6 illustrates in a top planar view, the rotatable selection ring 52. The ring 52, has a generally circular exterior peripheral surface 90. The peripheral surface 90 is interrupted by a plurality of spaced-apart, finger grippable depressions 92. The depressions 92 provide additional gripping surface so that the patient P can readily rotate the selection ring 52.

The ring 52 defines an internal cylindrical surface 94. Formed on the interior cylindrical surface 94 are three inwardly extending flange members 96a, 96b and 96c (illustrated in phantom). The members 96a through 96c are spaced apart on 120 degree intervals so as to slidably engage the axially-oriented slots 66 in the upper cylindrical portion 60 of the base 50 at the insertion-removal location.

Interspaced between the inwardly extending flanges 96a through 96c are three spaced apart, orientation identifying flanges 100, 102 and 104 (illustrated in phantom). The flanges 100 and 102 correspond to the slots 70 and 72 of the base member 50. The inwardly extending offset flange 104 matches the offset slot 74 in the base 50 when the cylindrical selection ring 52 is oriented at its insertion-removal position.

Due to the offset of the flange 104 and the slot 74, the selection ring 52 can only be engaged with the base 50 at this single, predetermined, insertion-removal position. Subsequent to positioning the selection ring 52 on the base member 50 and rotating the selection ring in the direction 54, each of the inwardly extending flanges 96a through 96c and 100 through 104 slidably engages the lower surface 62a of the discontinuous annular flange 62. Hence, the selection ring 52 cannot be removed from the base 50 until it is returned to its initial insertion-removal position.

Figure 7:
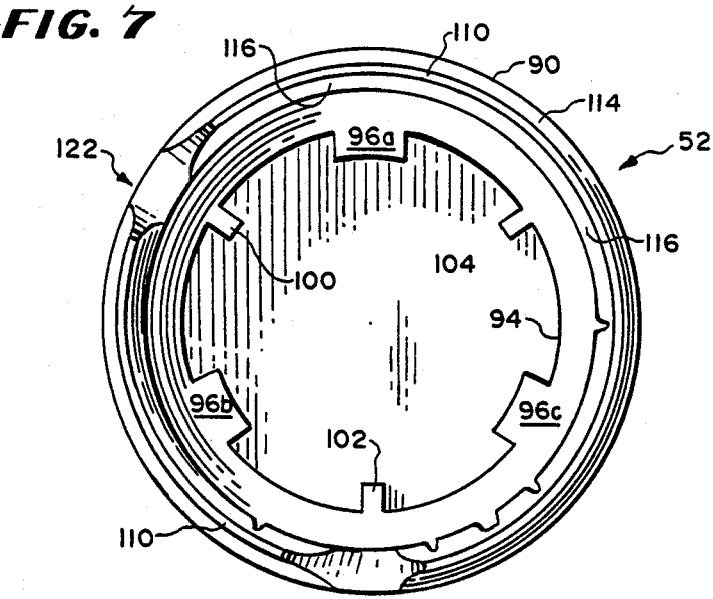
FIG. 7 is a bottom plan view of the rotary selection member of FIG. 6.

FIG. 7, a bottom plan view of the selection ring member 52 further illustrates the relative relationships of the flanges 96a through 96c and 100 through 104. In addition, a discontinuous annular surface 110 is formed along a lower edge 112 of the rotatable selection member 52. The discontinuous annular surface 110 is positioned between first and second biased surfaces 114 and 116.

The discontinuous annular surface 110 cooperates with the deformable member, either 84 or 86 as illustrated in FIG. 5, to externally apply clamping forces to sections of one or more of the tubing members 20, 24 and 26 extending through the slots 68 for the purpose of blocking fluid flow there-through.

Two valve openings, or discontinuities, 120 and 122 are spaced 120 degrees apart from one another in the surface 110. The discontinuities 120, 122 provide openings for the purpose of relieving the clamping force applied to the respective tubing member and permitting the flow of fluid therethrough.

The tubing members 120, 122 and 126 extend through respective slots 66 at spaced apart 120 degree angles. Hence, a maximum of two tubing members can be unclamped for fluid flow communication using the exemplary valve system 14. It will be understood that the precise number of discontinuities in the annular surface 110 is not a limitation of the present invention.

Figure 8:
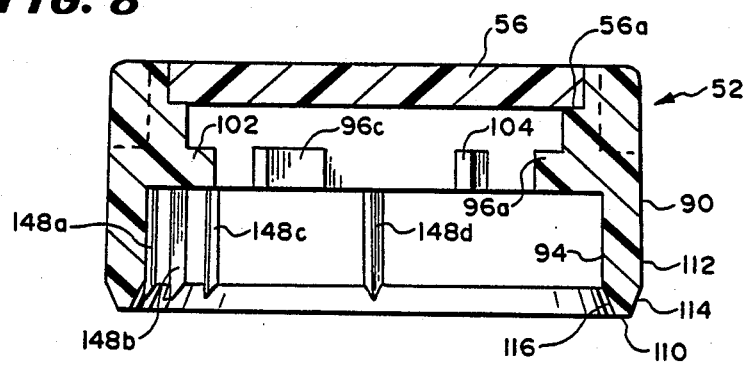
FIG. 8 is a view in section of the rotary selection member taken along plane 8-8 of FIG. 6.

FIG. 8 illustrates a sectional view of the rotary selection ring 52 taken along plane 8—8 of FIG. 6. The clamping annular surface 110 is positioned between the two biased surfaces 114 and 116. A lip 56a is provided upon which the cap 56 rests. The cap 56 can be fixedly attached to the ring 52 in any one of a variety of ways including screws, pins or adhesive.

FIGS. 9A–9D fragmentary, enlarged views illustrate the shape of the valve openings 120, 122. In addition FIGS. 9A–9D illustrate the process of unclamping and reclamping a tubular member such as the member 22. Valve opening 120 is illustrated and it is identical to valve opening 122. In addition, the rotating interrelationship between selection ring 52 and base member 50 is illustrated.

An exemplary section of the hollow tubing member 22 is illustrated with respect to the valve opening 120. Adjacent the tubing member 22 is a deflected section 84a of the deformable O-ring 84 which is in turn positioned adjacent the lower surface 82a of the annular slot 82.

The illustrated valve opening 120 is formed with a first convex circular surface 126 of a radius on the order of 0.120 inches. The surface 126 smoothly engages a concave surface 128 with radius on the order of 0.135 inches. The surface 128 terminates in a surface region 130 oriented at a 45° angle with respect to the annular ring 110. The surface 130 rejoins the annular ring 110 via a gently curved region 132 of radius on the order of 0.135 inches.

Figure 9A:
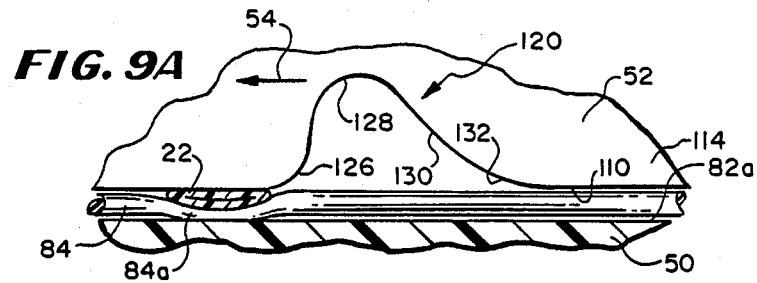
FIGS. 9A through 9D are enlarged fragmentary views illustrating the cooperation between the base member and the selection member as the selection member is rotated to unclamp and then clamp a tubing member.
Figure 9B:
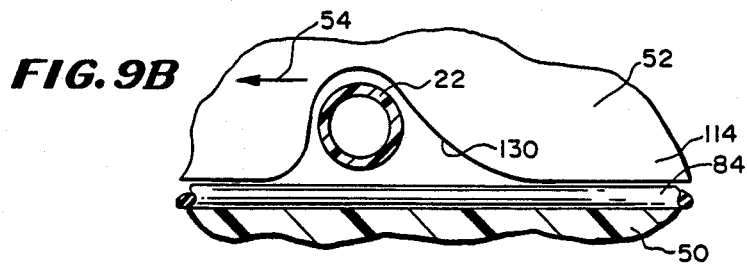

In FIG. 9A, the tubing member 22 is shown clamped against the region 84a of the deformable member 84. The member 84 is slightly deformed in the region 84a. As the selection ring 52 is rotated in the direction 54, the valve opening 120 unclamps the tubing member 22 as illustrated in FIG. 9B permitting a flow of fluid therethrough. The relative position of the base 50 and selection ring 52, as in FIG. 9B, corresponds to one of a plurality of predetermined flow defining index positions.

Figure 9C:
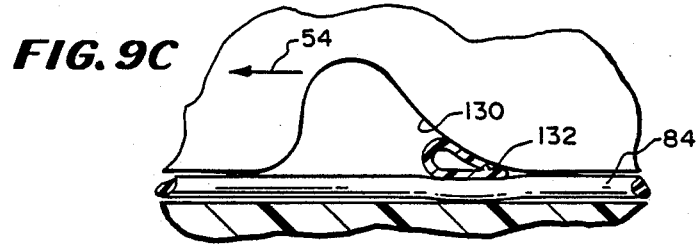
Figure 9D:
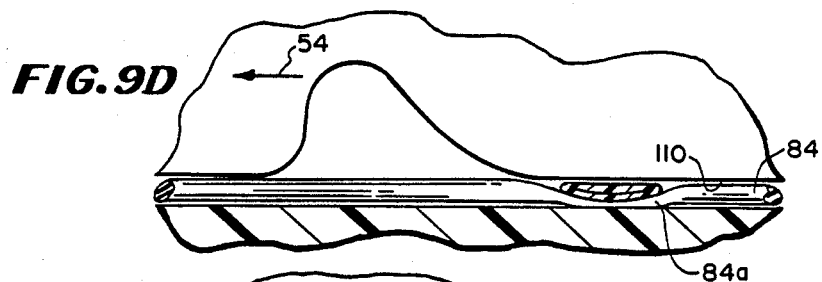

As the rotary selection member 52 is rotated in the direction 54, the planar surface 130 slidably engages the tubing member 22 forcing that member against the deformable O-ring 84 as illustrated in FIG. 9C. As rotation of the selection member 52 continues, the tubing member 22 slidably engages the transition surface 132, and then finally is again clamped shut between the discontinuous annular surface 110 and the slightly deflected region 84a of the O-ring 84 as in FIG. 9D.

Figure 9E:
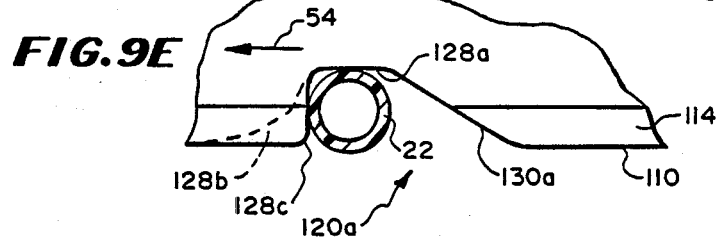
FIG. 9E is an enlarged fragmentary view of an alternate valve opening.

FIG. 9E illustrates an alternate valve opening 120a. The valve opening 120a is formed with a planar surface 128a as opposed to the circular surface 128. In addition, the planar terminating surface 130a intersects the annular clamping surface 110 without an intervening convex surface such as the surface 132.

As a further alternate to the illustrated valve openings of FIG. 9E, an opening can be formed with a biased surface 128b, illustrated in phantom in FIG. 9E. Such a surface provides for a gradual release of the closure forces as the member 52 is rotated. In contrast, the stepped surface 128c shown in solid lines in Figure. 9E catches against the tubing 22 during movement of the selection member 52 in a direction opposite to the intended direction 54. The lodgment of the stepped surface 128c against the tubing 22 serves as a rachet, preventing movement of the selection member 52 in this unintended opposite direction.

FIG. 9A through 9D illustrate the cooperative interaction between the base member 50 and the rotary selection ring 52 as the ring 52 is rotated. As a result of this cooperative interaction, a closed or clamped tubing member 22 is unclamped so that fluid can flow therethrough. Then, as the selection member 52 is further rotated in the direction 54, the tubing member 22 is again clamped shut, blocking the flow of fluid therethrough.

Figure 10A:
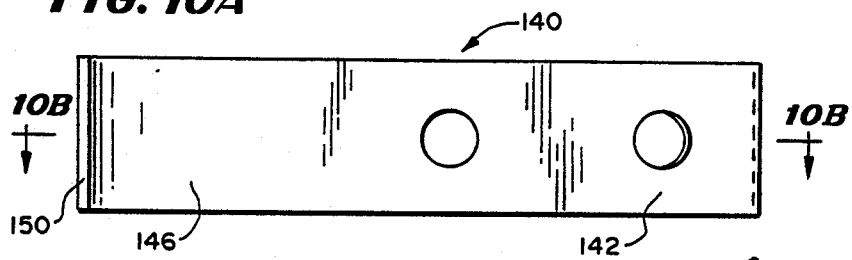
FIG. 10A is a front plan view of a spring biasing indexing member affixable to the base member of the valve system.
Figure 10B:
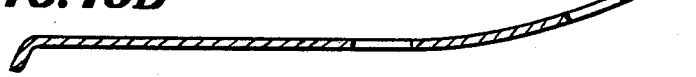
FIG. 10B is a view in section taken along plane 10B—10B of FIG. 10A.

FIGS. 10A and 10B illustrate a nonreversing indexing member 140 which provides for locking the rotary selection member 52 into one of a plurality of predetermined index locations, with respect to the base 50, as the member 52 is rotated. The indexing member may be variously constructed. For example, it can take the form of a rachet. In the illustrated embodiment, the indexing member 140 is spring biased. The spring member 140 has an end 142 which can be affixed to the base member 50 adjacent locating notch 144.

A free end 146 of the spring member 140 can slidably engage a plurality of slots, such as the slots 148a through d formed on the interior surface 94 of the selection member 52 (best seen in FIG. 8). The slots 148a through 148d are shaped such that a curved end region 150 of the end 146 can slide into and out of a respective slot as the selection member 52 is rotated in the direction 54.

However, when the curved end region 150 engages a respective slot, such as a slot 148c, the selection member 52 cannot be rotated opposite the direction 54. Hence, cooperation between the base 50 and rotary member 52, in combination with the position of the respective slots 148a through 148d define a plurality of predetermined index positions through which the selection member 52 can be rotated started from an initial insertion-removal position. Slot 148b, illustrated in FIG. 8, is larger than the other slots and the end region 150 engages that slot when the selection member 52 is inserted onto the base member 50 at the insertion-removal position.

Figure 11A:
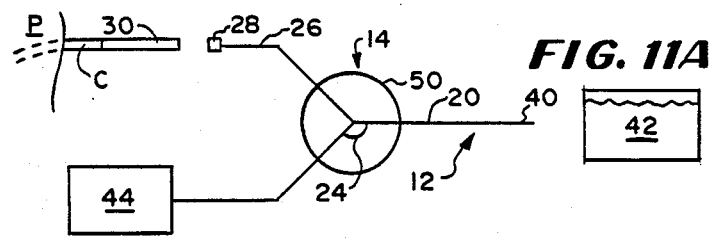
FIGS. 11A through 11F illustrate schematically a method of practicing peritoneal dialysis in accordance with the present invention.

FIGS. 11A through 11F illustrate schematically a method of carrying out a peritoneal dialysis drain and fill cycle in accordance with the present invention. The set 12 and the valve system 14 are illustrated schematically in FIGS. 11A through 11F. In FIG. 11A the set 12 is mounted on the base 50 with the keyed Y junction 24 engaging the mating portion of the base 50. An empty dialysis solution container 44 is shown affixed to the conduit 22 which will be used as the drain line. A full dialysis solution container 42, containing fresh solution, is shown adjacent the distal end 40 of the line 20 which will be used as the fill line. The distal end of the line 26 with connector 28 is shown adjacent the end of the connection set 30 which is coupled to the catheter C of the patient P.

Figure 11B:
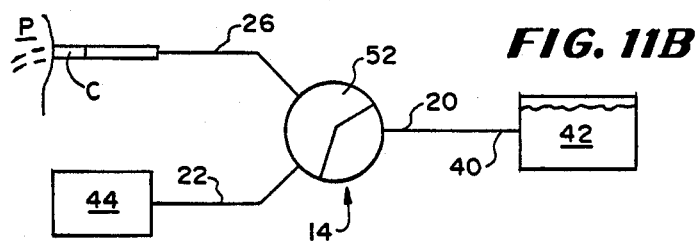

FIG. 11B illustrates the valve system 14 with the rotary selection member 52 mounted thereon and positioned in a first index position. In the first index position, tubing members 20, 22 and 26 are all clamped shut. Further, the fresh bag of dialysis solution 42 has been coupled to the distal end 40 of the tubing member 20. The tubing member 26, via the connection set 30 has been coupled to the external end of the catheter C.

Figure 11C:
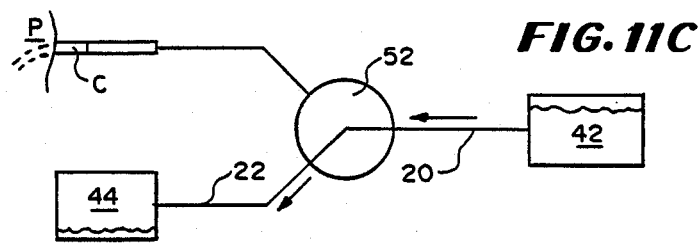

FIG. 11C illustrates schematically a flush sequence with selection member 52 having been rotated to a second index position. Tubing member 20 has been placed in fluid flow communication with line 22 permitting a flushing flow of fresh fluid from the container 42 of dialysis fluid to the empty container 44. Arrows along the tubing members 20 and 22 indicate a direction of fluid flow. The flush operation can continue on the order for 5 to 10 seconds or so.

Figure 11D:
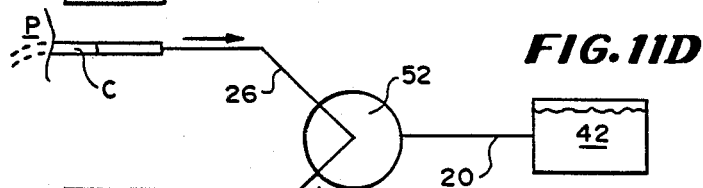

FIG. 11D illustrates selection member 52 having been rotated to a third index position wherein tubing members 26 and 22 are placed in fluid flow communication. Fluid in the peritoneal cavity of the patient P can then flow through the catheter C and, via the lines 26 and 22, drain into the essentially empty dialysis solution container 44. The container 44 then becomes filled with drained or spent dialysis solution. The drain portion of the cycle takes place under the flow of gravity and continues for about 15-20 minutes.

Figure 11E:
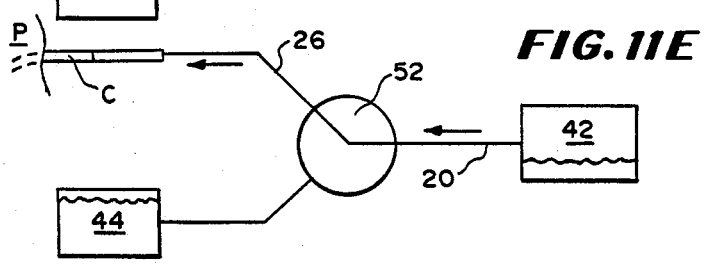

FIG. 11E illustrates the selection member 52 having been rotated to a fourth index position wherein the tubing member 20 is placed in fluid flow communication with the tubing member 26 in order that fresh dialysis solution can flow from the container 42, through patient's catheter into the patient's peritoneal cavity. The fill portion of the cycle takes place under the influence of the force of gravity and takes on the order of 10-15 minutes.

Figure 11F:
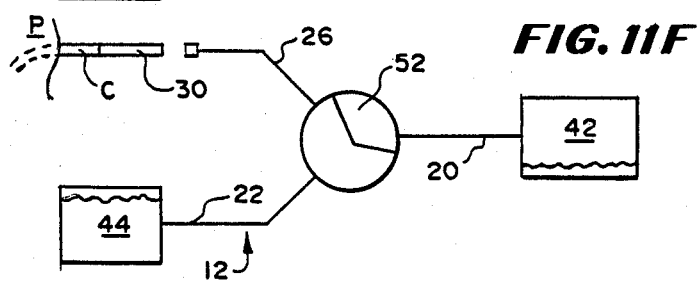

FIG. 11F illustrates the selection member 52 having been rotated to a fifth index position wherein the fluid flow lines 20, 22 and 26 are all clamped shut. In this position the container 42, which originally contained fresh dialysis solution, is essentially empty. The container 44 which started as an empty container is essentially filled with spent dialysis solution. The tubing member 25 is now disconnected from the connection set 30 and the patient's catheter C. The drain and fill cycle has beem completed.

It is only necessary to remove the selecting member 52 from the base 50 by rotating it from the 5th index position to the insertion-removable position. The member 52 can than be removed from the base 50 and the patient P can dispose of the set 12. The valve system 14 can then be returned to storage until the end of the dwell period when it is time to carry out the next drain and fill cycle. If a reusable set is being used, it is placed in storage until the end of the dwell period.

Figure 12:
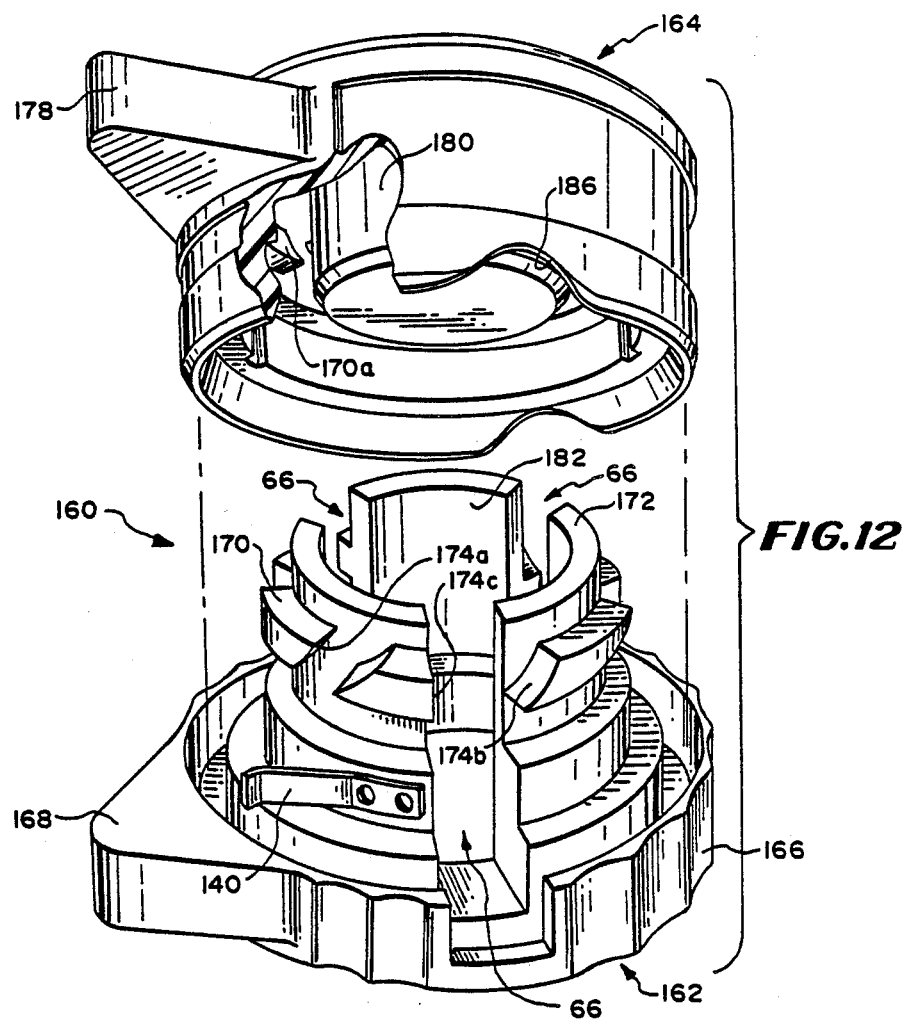
FIG. 12 is an enlarged perspective view, partly broken away, of an alternate embodiment of the present valve system.
Figure 13:
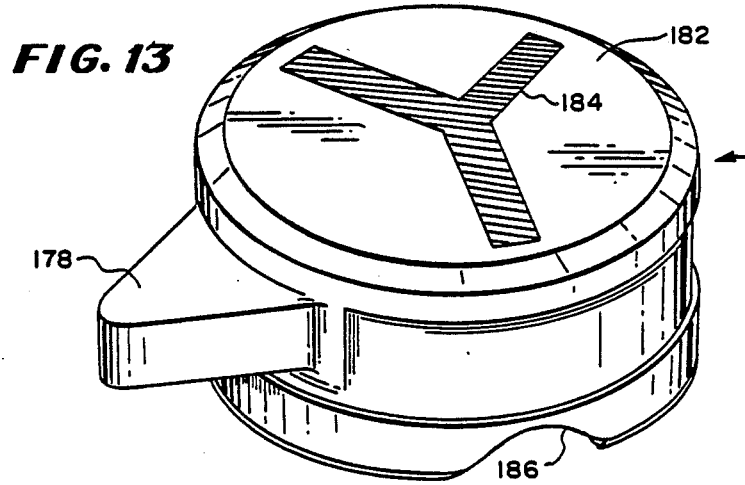
FIG. 13 is a perspective view of the selecting member illustrating a fluid flow indicator thereon.

FIG. 12 illustrates an alternate embodiment 160 of the present fluid flow control valve. The valve 160 includes a base member 162 and a rotary selection member 164.

The base member 162 is similar to the base member 50. However, the base member 162 is somewhat modified. The base member 162 includes a plurality of gripable surfaces 166 positioned about an exterior peripheral surface thereof. In addition, a gripable projection or lobe 168 has been affixed to one side of the base member 162.

A set of discontinuous threads 170 is provided spaced about a cylindrical body portion 172 of the base member 162. The threads 170 are angled such that the selecting member 164 can be threaded onto and screwed down onto the base member 162. The selecting member 164 carries a set of matching threads 170a.

Each of the discontinuous threads 170 has a biased surface 174a which slideably engages a corresponding surface positioned on the threads 170a in the selecting member 164 as the selecting member is being rotated onto the base member 162. This cooperative interaction draws the selecting member 164 down onto the base 162 and simultaneously crimps the tubing members 26 closed as the member 164 is rotated. Each of the discontinuous threads 170 terminates in a biased surface 174b.

The surface 174b provides clearance for the threads 170a carried on the selecting member 164. Some threads 170 terminate adjacent the slots 66 at axially oriented surfaces 174c. The axially oriented surfaces 174c are essentially perpendicular to the plane of rotation of the member 164.

Further, the selecting member 164 includes a manually gripable projection or lobe 178 corresponding to the projection 168 affixed to the base member 162. A cylindrically shaped alignment member 180 has been provided within the selecting member 164. The cylindrical alignment member 180 slideably engages an interior peripheral surface 182 of the cylindrical member 172. This engagement occurs prior to the engagement of the threaded members 170 with the corresponding threaded members 170a in the selecting member 164.

The selecting member 164 also includes on a top surface 182 a flow diagram 184 useable to indicate which tubing members are open and which tubing member is clamped shut. This provides a visual indicia of the expected direction of fluid flow to assist the user.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A multi-position mechanical apparatus for controlling fluid flow within a fluid transfer device having multiple, interconnected flexible, conduits normally open for fluid flow therethrough, the apparatus comprising:
   a base member for receiving a plurality of the interconnected fluid flow conduits; and
   selecting means, including a rotatable member rotatable in only one direction, said selecting means removably affixable to said base member and supported movably by said base member for selectively blocking fluid flow through at least one of the members of the plurality of flexible fluid flow conduits, said selecting means being affixable to said base member only at a single rotational insertion/removal position.

2. An apparatus as in claim 1 wherein said selecting means includes means for applying a clamping force to at least the one member of the plurality thereby temporarily deflecting a portion thereof closing the fluid flow pathway therein.

3. An apparatus as in claim 2 wherein said selecting means includes means for indexing through a predetermined sequence of positions thereby clamping shut in said predetermined sequence selected members of the plurality of fluid flow conduits.

4. An apparatus as in claim 3 wherein said means for indexing defines a plurality of predetermined sequence positions angularly displaced from one another.

5. An apparatus as in claim 4 wherein said force applying means includes a surface for clamping shut selected members of the plurality of fluid flow conduits and at least one selectively shaped valve opening for selectively permitting fluid flow through at least one selected conduit associated with at least one sequence position.

6. An apparatus as in claim 4 wherein said force applying means includes a selectively shaped valve opening defined on said rotatable member for selectively permitting fluid flow through selected members of the plurality of fluid flow conduits associated with selected members of said plurality of predetermined sequence positions.

7. An apparatus as in claim 6 wherein said valve opening is formed with a first region, with a selected unclamped fluid flow conduit extendable therethrough, and with a shaped second region for slidably engaging the fluid flow conduit and for applying force thereto to clamp the conduit shut to block the flow of fluid therethrough as said rotatable member is rotated.

8. An apparatus as in claim 7 including a second valve opening defined on said rotatable member, spaced from said first valve opening, so as to unclamp a second fluid flow conduit simultaneously with unclamping the first fluid flow conduit permitting fluid flow therebetween.

9. An apparatus as in claim 8 wherein said indexing means includes a spring member, affixed at a first end to said base member, with a second member in slidable contact with said rotatable member so as to define said sequence of index positions.

10. An apparatus as in claim 6 wherein as said rotatable member rotates, said valve opening moves angularly from a first sequence position to a second sequence position in cooperation with said indexing means.

11. An apparatus as in claim 10 wherein said indexing means includes means for retaining said movable member at each selected sequence position.

12. An apparatus as in claim 11 wherein said retaining means exerts a predetermined retaining torque to retain said valve opening at each selected position with said valve opening movable to an adjacent, angularly displaced, position in response to an applied torque in excess of said retaining torque.

13. An apparatus as in claim 10 wherein said indexing means permits rotation of said rotatable member in a selected direction and includes means blocking rotation opposite said selected direction.

14. An apparatus as in claim 13 wherein said base member includes a plurality of spaced apart, conduit receiving apertures.

15. An apparatus as in claim 14 wherein each said conduit receiving aperture includes first and second spaced apart, surfaces joined by a third surface.

16. An apparatus as in claim 6 including a resilient member carried by said base member with said force applying means selectively clamping selected members of the plurality of fluid flow conduits against selected portions of said resilient member thereby blocking fluid flow therethrough.

17. An apparatus as in claim 16 wherein said resilient member is a circular member.

18. An apparatus as in claim 17 wherein said resilient member has an essentially square cross section.

19. An apparatus as in claim 18 wherein said resilient member is a gasket with a planar surface.

20. An apparatus as in claim 17 wherein said resilient member has an esentially circular cross section.

21. An apparatus as in claim 20 wherein said circular member is an O-ring.

22. An apparatus as in claim 16 wherein as said force applying means clamps at least one of the selected members of the plurality against a selected portion of said resilient member, said portion is deflected.

23. An apparatus as in claim 3 wherein said selecting means includes a linearly movable member and said means for indexing defines a plurality of predetermined sequence positions linearly displaced from one another.

24. An apparatus as in claim 23 wherein said force applying means includes at least one region for selectively applying conduit clamping force to at least one selected conduit associated with at least one sequence position blocking fluid flow therethrough.

25. An apparatus as in claim 24 wherein said force applying means includes a selected valve opening, carried by said linearly movable member for selectively removing conduit clamping force from selected members of the plurality associated with said plurality of predetermined sequence positions.

26. An apparatus as in claim 25 wherein as said movable member moves linearly, said valve opening moves linearly from a first sequence location to a second sequence location in cooperation with said indexing means.

27. An apparatus as in claim 26 wherein said indexing means includes means for retaining said movable member at each selected sequence position.

28. An apparatus as in claim 27 wherein said retaining means exerts a predetermined retaining force to retain said valve opening at each selective position with said opening movable to an adjacent linearly displaced position in response to an applied force in excess of said retaining force.

29. An apparatus as in claim 27 wherein said indexing means permits linear movement of said member in a selected direction and includes means blocking movement opposite said selected direction.

30. An apparatus as in claim 1 wherein said base member has a selectively oriented, cylindrical member with a threaded end; and said selecting means being threaded for engagement with said threaded end of said cylindrical member.

31. A mechanical apparatus as in claim 30 including a cylindrical alignment member, carried by said selecting means and slidably receivable within said threaded cylindrical member as said selecting means moves toward said base.

32. A mechanical apparatus as in claim 30 with said threaded end including a plurality of spaced apart biased surfaces to pull said selecting means axially toward said base member as said means is rotated onto said base member.

33. An apparatus as in claim 1 further comprising flow indicator means associated with said selecting means.

34. A multi-position rotary valve for controlling fluid flow within a fluid transfer device having multiple, interconnected, flexible conduits normally open for fluid flow therethrough, the rotary valve comprising:

a base member for receiving a plurality of interconnected fluid flow conduits; and selecting means removably, and rotatably mountable on said base member for clamping shut selected of the fluid flow conduits with said selecting means defining at least one rotatably movable valve opening for unclamping selected of the fluid flow conduits and, permitting a flow of fluid therethrough as said selecting means is rotated, said selection means being rotatable in only one direction and mountable on said base only at a single rotational insertion/removal position.

35. A valve as in claim 34 wherein said base includes means for orienting the fluid transfer device such that said device can be properly positioned on said base with only a single orientation.

36. A valve as in claim 35 wherein said means for orienting is centrally located with respect to said base.

37. A valve as in claim 36 wherein said orienting means includes at least one region bounded in part by an arcuate surface.

38. A valve as in claim 37 wherein said orienting means includes a second region, spaced from said one region, bounded in part by an arcuate surface.

39. A valve as in claim 38 wherein said arcuate surface of said second region extends at least through an angle on the order of 60°.

40. A valve as in claim 37 wherein said arcuate surface extends through an angle on the order of 120°.

41. A valve as in claim 35 wherein said base member carries a discontinuous annular flange with said selecting means including a plurality of spaced apart, radially extending members for slidably engaging said discontinuous annular flange as said selecting means is rotated thereby rotatably locking said selecting means to said base member.

42. A valve as in claim 41 wherein said selecting means includes annular sliding means for clamping selected of the fluid flow conduits against at least one region of said base member.

43. A valve as in claim 41, wherein said annular sliding means includes an annular surface interrupted by said valve opening.

44. A valve as in claim 43, wherein said annular surface is interrupted by a second valve opening spaced from said valve opening.

45. A valve as in claim 44 wherein said two valve openings are spaced about 120° from one another.

46. A valve as in claim 43 wherein said valve opening includes a first region through which a section of a selected conduit can extend without being clamped shut.

47. A valve as in claim 46 wherein said valve opening includes a second region adjacent said first region, for slidably engaging the section of the selected conduit and for gradually forcing the section against a part of said base region thereby clamping the conduit shut and blocking the flow of fluid therethrough as said selecting means is rotated.

* * * * *